(12) United States Patent
Guyette et al.

(10) Patent No.: US 10,919,019 B2
(45) Date of Patent: Feb. 16, 2021

(54) APPARATUS FOR THE SYNTHESIS OF RADIOPHARMACEUTICAL PRODUCTS

(71) Applicant: Ion Beam Applications S.A., Louvain-la-Neuve (BE)

(72) Inventors: Michel Guyette, Namur (BE); Jozef Comor, Belgrade (RS)

(73) Assignee: Ion Beam Applications S.A., Louvain-la-Neuve (BE)

( * ) Notice: Subject to any disclaimer, the term of this patent is extended or adjusted under 35 U.S.C. 154(b) by 640 days.

(21) Appl. No.: 15/729,620

(22) Filed: Oct. 10, 2017

(65) Prior Publication Data

US 2018/0099261 A1    Apr. 12, 2018

(30) Foreign Application Priority Data

Oct. 11, 2016 (EP) ..................... 16193281

(51) Int. Cl.
| | | |
|---|---|---|
| *B01J 19/00* | (2006.01) | |
| *B01J 19/18* | (2006.01) | |
| *A61K 51/00* | (2006.01) | |

(52) U.S. Cl.
CPC ............. *B01J 19/18* (2013.01); *A61K 51/00* (2013.01); *B01J 19/004* (2013.01)

(58) Field of Classification Search
CPC ........ B01J 19/004; B01J 19/08; B01J 19/081; B01J 2219/00927; C07B 59/00; C07B 59/002; C07B 59/005; C07B 2200/05
See application file for complete search history.

(56) References Cited

U.S. PATENT DOCUMENTS

| 7,235,216 B2 | 6/2007 | Kiselev et al. |
| 2006/0245980 A1 | 11/2006 | Kiselev et al. |
| 2013/0170931 A1 | 7/2013 | Samper et al. |

FOREIGN PATENT DOCUMENTS

| EP | 1 343 533 B1 | 8/2004 |
| EP | 2 022 736 A1 | 2/2009 |
| WO | WO 2014/160799 A1 | 10/2014 |
| WO | WO 2016/146686 A1 | 9/2016 |
| WO | WO 2016/146693 A1 | 9/2016 |

OTHER PUBLICATIONS

European Search Report dated Dec. 7, 2016, 4 pages.

*Primary Examiner* — Jill A Warden
*Assistant Examiner* — Dwayne K Handy
(74) *Attorney, Agent, or Firm* — Finnegan, Henderson, Farabow, Garrett & Dunner LLP

(57) ABSTRACT

The present disclosure relates to an apparatus for the synthesis of chemical compounds, e.g., radiopharmaceutical compounds. In one implementation, the apparatus may include a synthesis module and a loading module configured to receive multiple chemical cassettes having reagents and a transfer mechanism. The apparatus may further include a shifter configured to move the cassettes from a location on the loading module to a location connected to the synthesis module on an interface configured to connect to the cassette.

18 Claims, 5 Drawing Sheets

APPARATUS FOR THE SYNTHESIS OF RADIOPHARMACEUTICAL PRODUCTS

CROSS-REFERENCE TO RELATED APPLICATIONS

This application claims the benefit of priority to European Application No. 16193281.9, filed Oct. 11, 2016, the contents of which are incorporated herein by reference.

TECHNICAL FIELD

The present disclosure relates to a device for synthesis of radiopharmaceutical products from radioactive compounds and/or chemical reagents located on cassettes or disposable cassettes.

The present disclosure relates, more specifically and without limitation, to a device for synthesis of radiopharmaceutical products, said device being able to perform multiple runs to produce radiopharmaceutical products, without human intervention.

BACKGROUND

In diagnostic modalities, such as Positron Emission Tomography (PET), Single Photon Emission Tomography (SPECT), and therapeutic applications radiopharmaceutical or radiochemical compounds are generally used, which are labelled by means of radioactive elements, such as $^{11}C$, $^{13}N$, $^{15}O$, $^{18}F$, $^{68}Ga$, $^{177}Lu$, $^{90}Y$, $^{89}Zr$, $^{64}Cu$, $^{124}I$, $^{123}I$ and many others for imaging and therapeutic purposes. The synthesis of these radiopharmaceutical compounds is often performed in apparatuses that enable the different chemical compounds located on a cassette to be brought into contact and heated, when applicable, during synthesis reactions.

During the synthesis process, four major issues may arise. The first issue concerns the handling of the compounds. The compounds comprise radioactive substances, which may be harmful for the humans that handle the synthesis apparatus. To avoid risk associated with the handling of radioactive products, the apparatuses are generally placed in a confined and shielded environment. These apparatuses are usually driven automatically, which may command the various operations enabling the synthesis, including the reaction, mixing, transfer, heating, and purification stages. The automation of these apparatuses generally reduces human error and human exposure to radioactivity.

The second issue concerns the quality and purity of the synthetized compounds. These products are usually injected into human beings for diagnostic or therapeutic applications. Therefore, to avoid any contamination issues and/or incorrect dosage of the reaction compounds, cassettes comprising all the reaction compounds in pre-metered bottles are sometimes used. Such cassettes may allow making a single run to produce a radiopharmaceutical compound or substance.

The third issue concerns the half-life of the synthetized products (for example, products containing $^{18}F$, $^{68}Ga$, etc.). Generally, radiopharmaceutical products have a short half-life and cannot be stored for later use. Therefore, it is often necessary to produce radiopharmaceuticals at regular intervals and to more efficiently use the apparatus during the day. It may be advantageous for syntheses to be performed successively ("back-to-back" runs). However, compact automated synthesizers often have a single interface between the cassette and the synthesizer. Moreover, cassettes are often disposable, allowing a limited number of syntheses runs. Hence, after a limited number of syntheses runs occur, the human operator usually must open the confined and shielded environment, remove the cassettes from the apparatus, and add new cassettes in order to start production again. This may be dangerous, due to the radioactivity surrounding the synthesis apparatus. Moreover, this may lead to possible human errors. Generally, the less the human operators intervene during the synthesis process, the lower the probability of making mistakes and/or introducing contaminations. One current solution uses more than one synthesis machine within the limited shielded environment. However, such a solution is unsatisfactory when the space available is constrained. Another solution is the re-use of disposable cassettes designated for a single-run, typically requiring a washing procedure, which may jeopardize the overall quality of the final product. In addition, due to the particularly short half-life of some of the isotopes incorporated into the radiopharmaceutical compounds, it may be necessary to avoid any loss of time (e.g., time used for the washing procedure) for producing a needed product.

The fourth issue concerns the flexibility of use of the synthesis apparatus. Generally, with a single synthesis apparatus, it is not possible to program and synthetize a range of different radiopharmaceutical compounds without human intervention. For example, when different radiopharmaceutical compounds need to be synthetized, an operator usually must manually add a new and different cassette to the apparatus, after a first run, for the synthesis of a new product.

Extant apparatuses tend to address only a subset of the four issues mentioned above. For example, European patent No. 1343533 and U.S. Pat. No. 7,235,216 generally relate to an apparatus and a cassette creating a reduced risk of contamination or incorrect dosages. The apparatus may comprise a lead chamber to reduce safety risks for the human handling of the synthesis processes. However, when multiple runs must be performed in a short interval, the issues mentioned above are not resolved. For example, the loading of the cassette onto the synthesis apparatus still is performed manually by an operator, exposing the operator to the residual radioactivity when he opens the shielded environment.

SUMMARY

To, at least partially, solve the issues mentioned above, embodiments of the present disclosure include a synthesis apparatus that may perform a plurality of synthesis runs in a safe and secured manner, without any human intervention during the plurality of synthesis. Embodiments of the present disclosure include an apparatus for the synthesis of radioactive products, e.g., radiopharmaceutical products, from radioactive elements, which may be used in a safe manner. Once a human has prepared the apparatus for multiple synthesis runs, the apparatus may perform multiple runs successively without the need of human intervention. Embodiments of the present disclosure also include an apparatus which may minimize the risk of contamination of the synthetized products, while assuring the safety of humans handling the synthesis product. While providing multiple consecutive synthesis runs, embodiments of the present disclosure may synthesize different products consecutively with the same apparatus, without human intervention between the consecutive runs. Consecutive runs may thus result in different products, depending on which cassettes have been loaded.

According to one aspect of the present disclosure, an apparatus for manufacturing of radiopharmaceutical products from reagents may comprise a synthesis device and a loading device on which chemical systems, e.g., in the form of a plurality of cassettes, may be mounted, with the cassettes having a mechanism for transferring the chemical reagents.

The synthesis device may include an interface and an extractor configured to act on the transfer mechanism of the cassettes when the cassettes are connected to the interface.

The apparatus may further comprise a shifter configured to successively shift the plurality of cassettes from a storage position to a connected position onto the interface, and the synthesis device may further comprise an ejector configured to eject a disposable cassette connected to the interface.

Indeed, with an apparatus according to some embodiments of the present disclosure, the four issues mentioned above may be, at least partially, mitigated. The whole apparatus may be placed in a safe and shielded environment, and/or the whole apparatus may be self-shielded to avoid any emission of radioactivity outside of the synthesis apparatus. The plurality of runs may be performed within cassettes that have, for each run, the necessary reagents for the synthesis of the desired radiopharmaceutical compounds. No human intervention is generally necessary in between runs, leading to a safe production of the radioactive compounds and/or no harmful radiation exposure to the operator(s). Another advantage of some embodiments of the present disclosure may be that multiple syntheses of the same radiopharmaceutical compound may be performed, in embodiments when all of the cassettes are of the same kind. In addition, it may also be possible to perform syntheses of a range of different radiopharmaceutical compounds in embodiments when the cassettes are of different kinds. Hence, according to the needs of the patients for the radiopharmaceutical compounds, apparatuses of the present disclosure may allow for the production of various compounds in correlation with these needs. For example, if a number of patients need to receive the same radiopharmaceutical compound, a sufficient quantity may be produced without human intervention once the apparatus is loaded with the cassettes. On the other hand, when a number of patients need to receive different radiopharmaceutical compounds, a variety of these compounds may be produced without human intervention. It may therefore be possible to produce the same and/or different radioactive compounds without human intervention. With apparatuses of the present disclosure, the loading of each new cassette onto the synthesis apparatus between synthesis runs is generally automatic.

In some embodiments, the apparatus according to the present disclosure may have a shifter including a transfer device configured to successively transfer the cassettes from the storage position to a loading position located near the interface, and the apparatus may comprise a connector configured to securely connect the cassettes to the interface.

In such embodiments, the connection of each cassette to the interface located on the synthesis device may be secured, leading to a more reliable apparatus and/or avoiding any misconnection between the cassette and the interface.

In some embodiments, the apparatus according to the present disclosure may comprise a shifter configured to dispose a positioning wedge on the connector when the shifter shifts a cassette from the storage position to the loading position.

In such embodiments, the interaction between the shifter and the connector may ensure an even more reliable positioning and connection of the cassette.

BRIEF DESCRIPTION OF THE DRAWINGS

These and further aspects of the present disclosure will be explained in greater detail by way of examples and with reference to the accompanying drawings in which.

The drawings of the figures are neither drawn to scale nor proportioned. Generally, similar or identical components are denoted by the same reference numbers in the figures.

DETAILED DESCRIPTION

Figure 1:
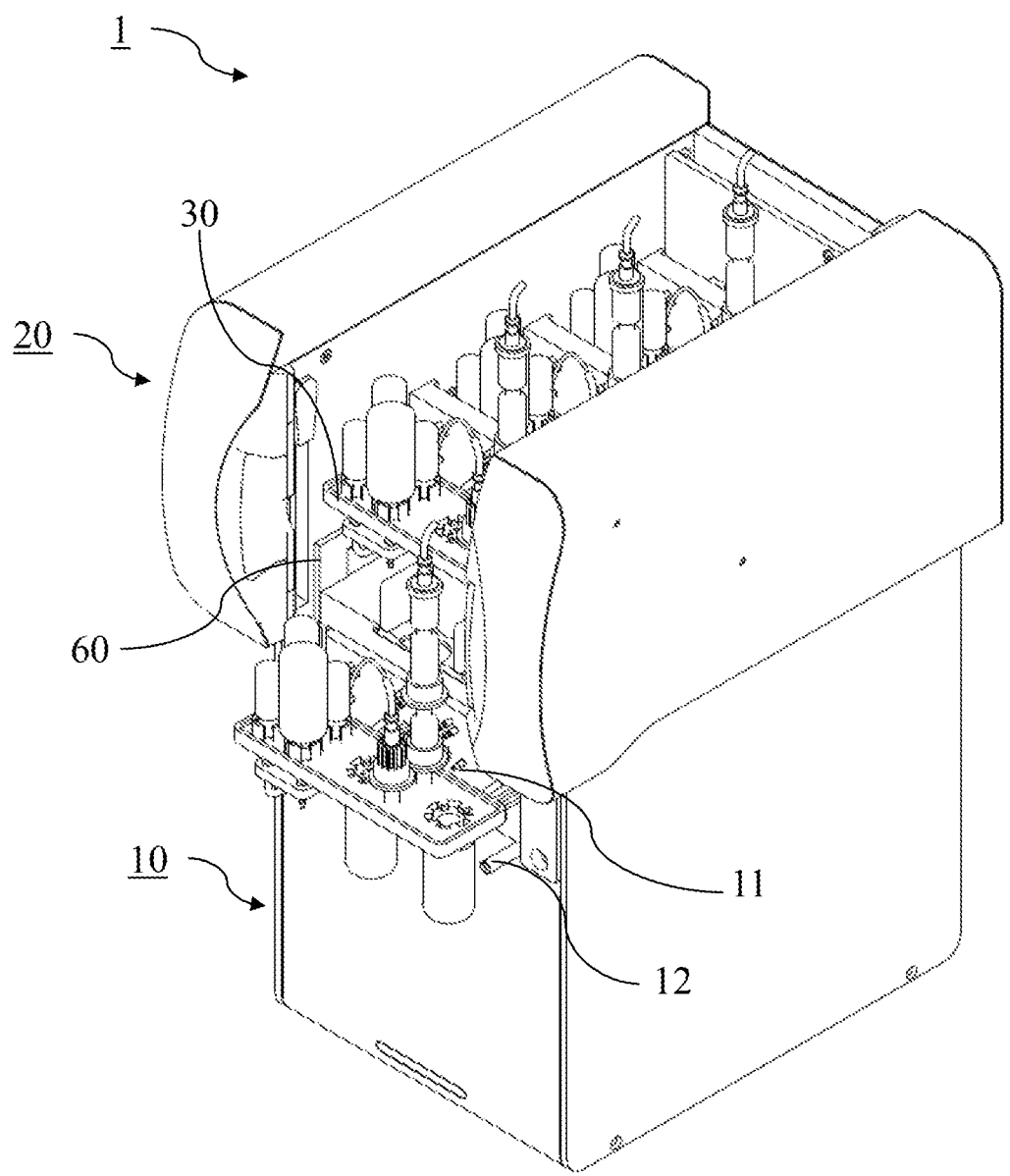
FIG. 1 schematically shows an apparatus according to one embodiment of the present disclosure, wherein the apparatus is loaded with several cassettes and a cassette is connected to the interface.

As illustrated in FIG. 1, the apparatus (1) according to some embodiments of the present disclosure may comprise a synthesis device (10) and a loading device (20). The apparatus may be able to produce radiopharmaceutical products from reagents, e.g., chemical reagents, when a cassette (30) is placed or fixed on an interface (11), and the apparatus (1) is in operation. The cassette may be a reusable cassette or a disposable cassette.

A cassette (30), also known as module, is a removable cassette generally known by those of ordinary skill in the art, which may be reusable, washable, and/or disposable after a single or several synthesis runs. In one embodiment, the cassette may be a disposable cassette, such as a single use disposable cassette. The cassette may be in the shape of a support and may contain chemical reagents, one or several reaction compartments, and/or a transfer mechanism between the chemical reagents and the reaction compartments. Such a cassette is generally discussed, for example, in European patent No. 1343533.

The cassette (30), on which transfer, reaction and purification functions may be performed and on which the chemical reagents and reaction compartments may be arranged, may be intended for association with the synthesis device (10) on the interface (11).

The interface (11) may be a fixed module located on the synthesis device (10), and a plurality of mechanical devices may be arranged thereon. The mechanical devices may be configured to cooperate with the transfer mechanism present on the disposable cassette (30) to allow the transfer of the reagents to the various reaction compartments. The various operations for synthesis of pharmaceutical products, including the actuation of these mechanical devices, may be commanded via automation. In other words, the apparatus (1), and more specifically the synthesis device (10), may be linked to a computer which may command the various operations enabling the performance of the synthesis, such as reaction and heating stages, and/or transfers of the reagents. This is generally discussed in European patent No. 1343533.

As illustrated in FIG. 1, the loading device (20) may be mounted over the synthesis device (10). In other embodiments, the loading device (20) may be mounted on other parts of, and/or next to, the synthesis device (10), for example, on one side of the synthesis device. In another embodiment, the loading device (20) may be placed outside of the shielded environment. In the embodiment depicted in FIG. 1, the loading device (20) may be mounted on the top of the synthesis device (10). The synthesis device (20) may be self-shielded and/or placed in a shielded environment (also known as a "hot cell"). In another embodiment, the apparatus (1) comprising the synthesis device (10) and the loading device (20) may be self-shielded (e.g., surrounded by lead plates and/or enclosed within a lead shield). In other words, the synthesis device and/or the entire apparatus may be enclosed within a shield reducing radiation emission outside of the shielded synthesis device and/or shielded apparatus.

A plurality of cassettes (30) may be mounted on the loading device (20). As illustrated in FIG. 1, the plurality of cassettes may be mounted on a rack (60) in a linear disposition, the cassettes being parallel to each other. The rack may have the form of two horizontal strips or bars on which the cassettes are placed. Other dispositions for the cassettes may be implemented by one of ordinary skill in the art. For example, the plurality of cassettes may be disposed on a carousel. In some embodiments, at least two cassettes may be placed on the loading device. In another embodiment, at least three cassettes may be disposed on the loading device. In yet another embodiment, at least four cassettes may be disposed on the loading device (20). The loading device (20) may have a different shape than that depicted in FIG. 1. For example, the loading device may be a circular platform such that the cassettes are not parallel to each other, but rather mounted on the circular platform like spokes.

The plurality of cassettes do not need to be identical regarding their chemical reagents content and/or their reaction compartments. The external edge of the plurality of cassettes (30) may have the same shape to cooperate with the loading device (20), but the content of the reagents may be different, for example, in embodiments when a diversity of radiopharmaceutical compounds have to be produced. In other embodiments, the plurality of cassettes (30) may be identical regarding their content, for example, in embodiments when a single radiopharmaceutical compound has to be produced by the synthesis device (10).

Figure 2:
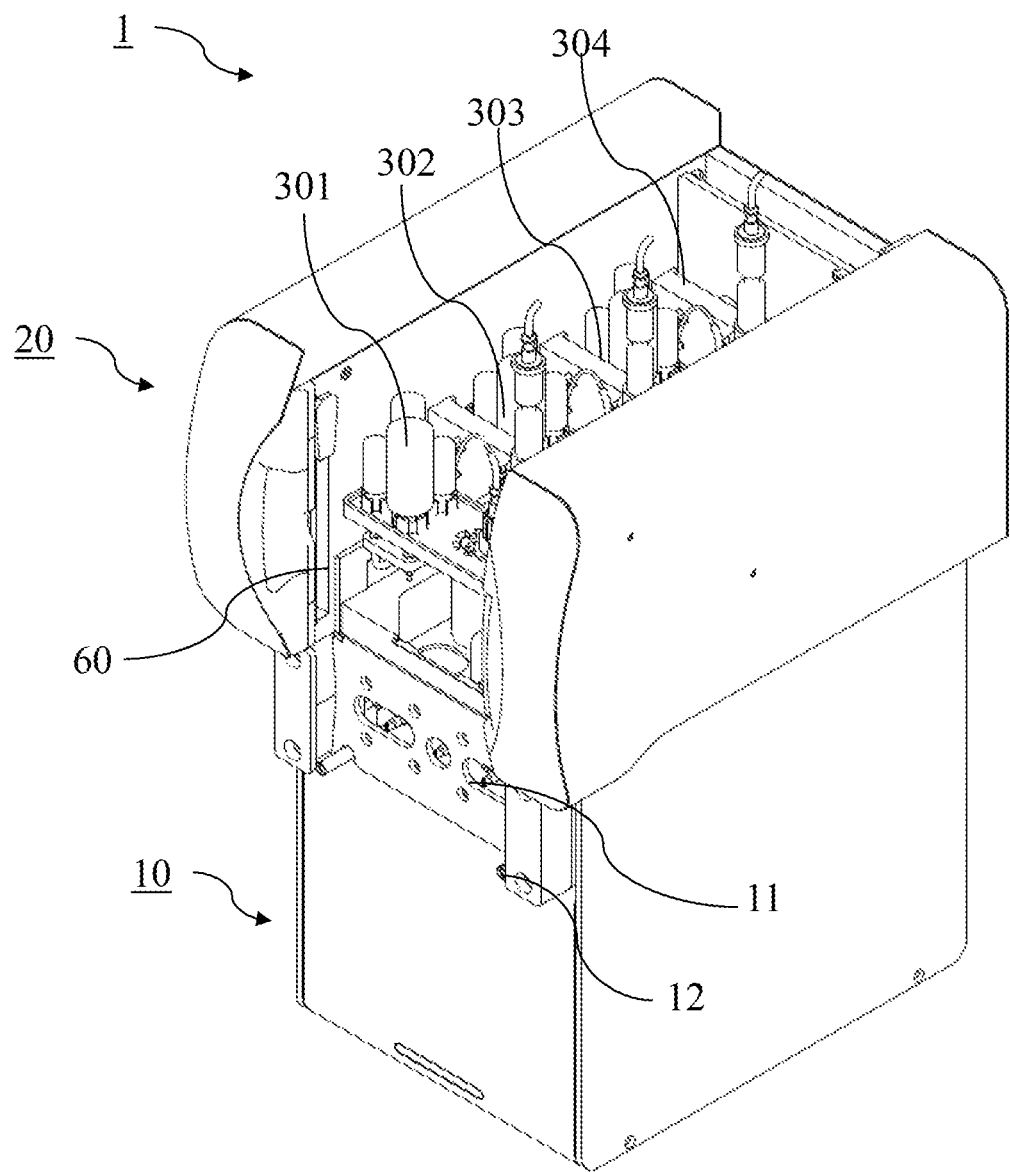
FIG. 2 schematically shows the apparatus of FIG. 1, wherein the cassettes are all disposed on the loading device.

When a person is preparing the apparatus according to the present disclosure for multiple runs to synthesize different products, he may place/put each cassette on the loading device, in the order intended for synthesis of the various radiopharmaceutical products. Once the cassettes are placed on the loading device (20), no direct human intervention may be needed for the loading, shifting, connection and/or ejection of each cassette. When a cassette is placed on the loading device (20), the cassette may be defined as being on its stacking or storage position. This is illustrated in the example of FIG. 2.

The apparatus (1) may comprise a shifter configured to successively shift the plurality of cassettes (30) from a storage position to a connected position onto the interface (11). As used herein, shifting refers to the movement of each cassette from a position where the cassette is placed on the loading device (20) in its storage position to the position where the cassette is functionally connected to the synthesis device (10) by way of the interface (11) (i.e., the connected position). The functional connection between the synthesis device (10) and a cassette is illustrated in the example FIG. 1. The shift from a storage position to a connected position onto the interface (11) may be performed by at least one shifter (32). This shifter may interact with an edge of the cassette and shift it from its storage position to the connected position. The function of the shifter (32) may be to successively move each cassette from its storage position (illustrated in the example of FIG. 2) to its connected position with the interface (11) (illustrated in the example of FIG. 1). The shifter (32) may be present on the loading device (20) and/or on the synthesis device (10). In one embodiment, the shifter may be fully present on the loading device (20).

A variety of shifters (32) may be implemented in apparatuses consistent with the present disclosure. For example, the shifter may be a piston or a hydraulic cylinder controlled by automation. When the piston or hydraulic cylinder is activated, it may shift the cassette from its storage position to the connected position. The shifting movement may be any kind of movement, like a rotation of the cassettes, a translation of the cassettes, a plurality of translations of the cassettes, or a combination between rotation and translation.

The shifter may be present on the synthesis device (10) and/or on the loading device (20). In one embodiment, the shifter may be fully located on the loading device (20) as illustrated, for example, in FIG. 4.

When the cassette is in its connected position, as illustrated in the example of FIG. 1, the synthesis of the radiopharmaceutical products may proceed. The synthesis device (10) may interact with the cassette connected to the interface (11) by way of mechanical devices (such as an extractor) as explained in paragraph [0022]. The whole interaction between the synthesis device (20) and the transfer mechanism on the cassette may be commanded by automation.

Figure 5:
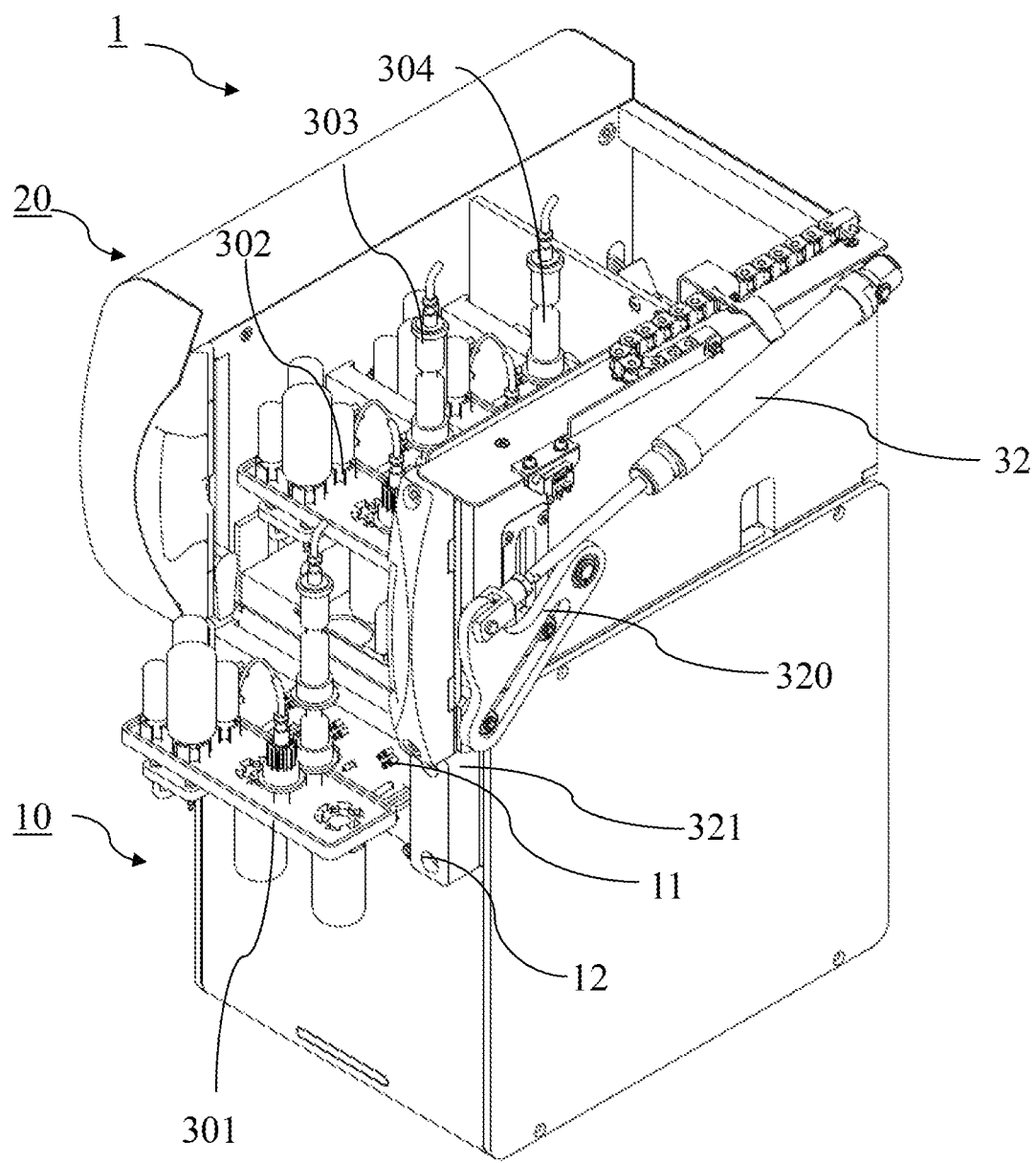
FIG. 5 schematically shows the apparatus of FIG. 2, wherein an example of the shifter is illustrated.

When the synthesis is over, the cassette connected to the interface (11) may be ejected. To this end, the synthesis device (10) may comprise an ejector configured to eject the cassette connected to the interface (11). This is illustrated in the example of FIG. 5. As illustrated, an ejector (12) is located near the interface (11). When the synthesis run is over, the ejector may be actuated and the cassette removed from the interface, and, for example, discarded into a shielded bin. The ejector may, for example, be a piston or a hydraulic cylinder that, when actuated, may allow for taking down or unhooking the cassette from the interface (11). The cassette may then fall into shielded bin. Once the cassette is ejected, the ejector may return to its original position.

Once the cassette used for a synthesis run is ejected from the interface (11), another cassette located on the loading device (20) in its storage position may be shifted from this position to the connected position of the interface (11).

Accordingly, as long as a cassette is present on the loading device (20), a new synthesis run may be performed after the ejection of the previous cassette, without any human intervention.

In one embodiment of the present disclosure, the shifter (32) may comprise a transfer device (320) and a connector (321). In this embodiment, the shifting of the cassette from its storage position to the connected position may comprise two movements. The first movement may be the movement of the cassette from its storage position, illustrated in the example of FIG. 2, to a loading position, illustrated in the example of FIG. 4. The loading position may be a position located nearby the interface (11), but the cassette is not connected to the interface (11). This movement may be achieved by the transfer device (320). The transfer device may, for example, be a piston or a hydraulic cylinder. When the piston or the hydraulic cylinder is activated, it may move the cassette from its loading position to the connected position. This movement may be any kind of movement, like a rotation of the cassettes, a translation of the cassettes, a plurality of translations of the cassettes, or a combination between rotation and translation. According to one embodiment, the second movement may be the movement of the cassette from the loading position to the connected position, as illustrated, respectively, in the examples of FIG. 2 and FIG. 1. This movement may be achieved by the connector.

It may allow for securing the connection between the cassette and the interface (11), thereby reducing risks of incorrect connection between the cassette and the interface, e.g., to avoid damages to the cassette and/or to the interface (i.e. the mechanical devices located on the interface) and/or to ensure the synthesis process will take place effectively. As an example, this tight and accurate movement of the connector may ensure correct interaction between the cassette and the interface (11) and may avoid any leaks of the reagents after connection.

Figure 4:
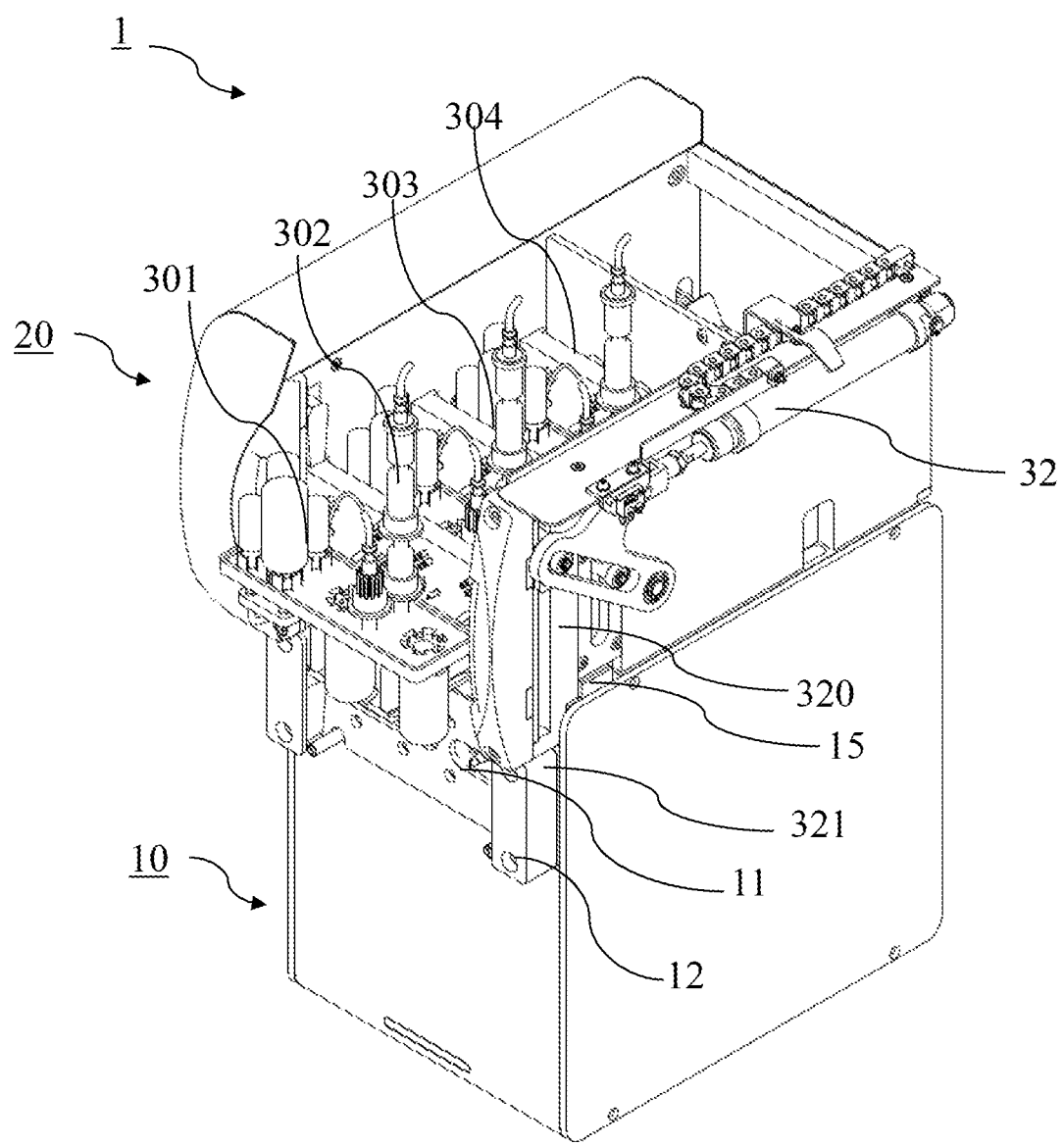
FIG. 4 schematically shows the apparatus of FIG. 1, wherein an example of the shifter is illustrated.

The connector may, for example, be a piston or a hydraulic cylinder that translates the cassette from the loading position to the connected position, as illustrated in the example of FIG. 4. In one embodiment, the movement from the loading position to the connected position may be a single translation movement. This simple movement may ensure an easy and accurate connection between the interface (11) and the cassettes.

In one embodiment of the present disclosure, the connector may be located on the synthesis device (20), e.g., near the interface (11). In one embodiment, the ejector and the connector may be configured to eject a cassette when it is connected to the interface (11) and may be configured to securely connect the cassette when it is in the loading position. The connector may be a piston or a hydraulic cylinder. In one embodiment, the connector may be a double acting hydraulic cylinder.

Figure 3:
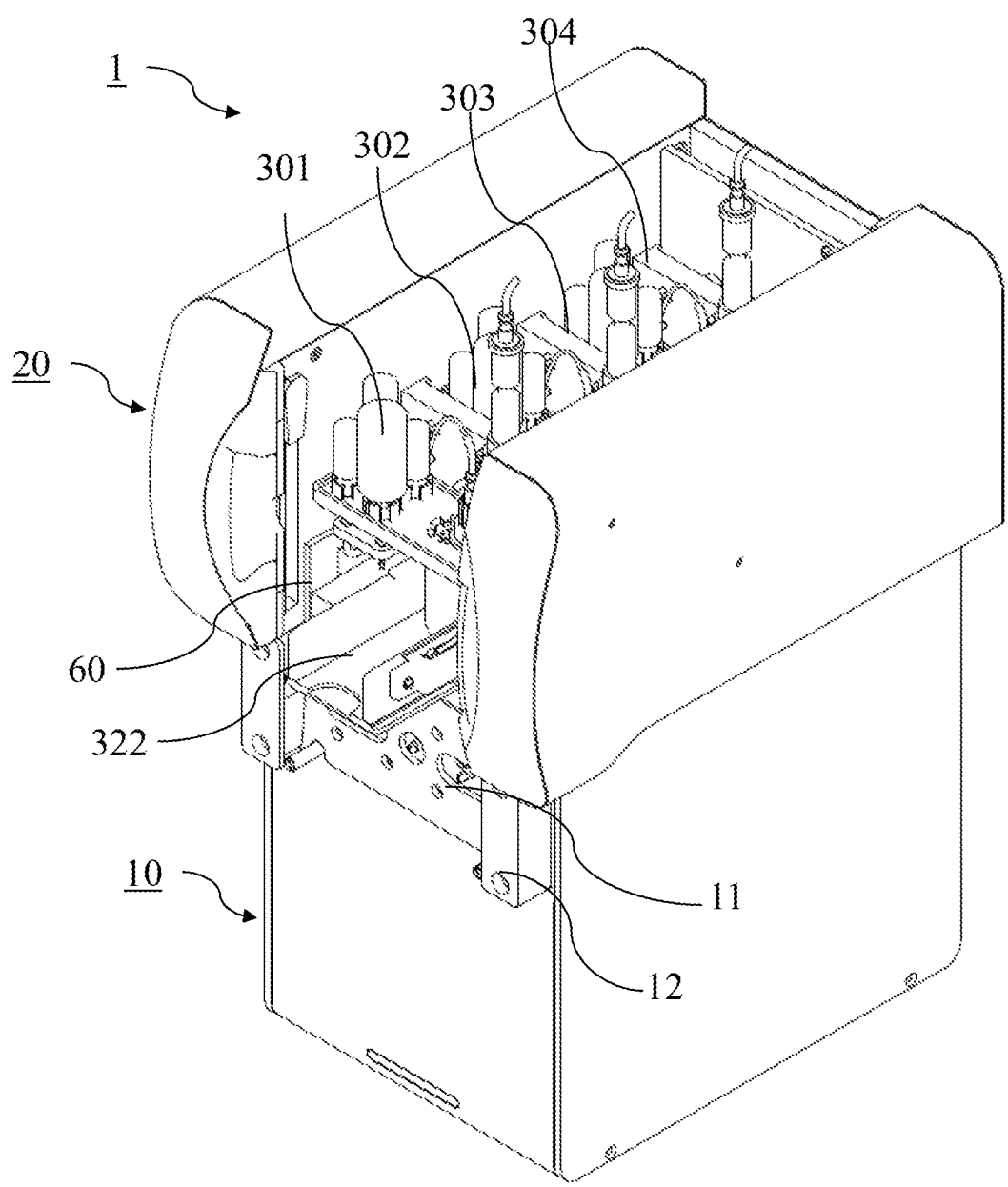
FIG. 3 schematically shows the apparatus of FIG. 1, wherein an example of a placement mechanism is illustrated.

In one embodiment of the present disclosure, the shifter (32) may also comprise a placement mechanism (322). This is, for example, illustrated in the example of FIG. 3. The placement mechanism (322) may be configured to successively place the cassettes from a stacking position to the storage position, both located, for example, on the loading device (20). In a more general embodiment, these two positions may be the same. In one embodiment, each cassette may be successively moved from its stacking position, i.e., the position where it has been placed on the loading device (20) before the apparatus begins to run a plurality of syntheses, to the storage position, already defined earlier, i.e., the position where the cassette is shifted through the connected position. As an example, illustrated in FIG. 2, the cassettes may be placed parallel to each other on a rack. As depicted, the first cassette (301) is in its storage position, while the three other cassettes (302, 303, 304) are in their stacking position. Once the first cassette (301) shifts from the storage position to the connected position, the second cassette (302) may move from its stacking position to the storage position. This movement may occur during the shifting movement of the first cassette, but it may also occur after the first cassette (301) has been ejected by the ejector (12), as illustrated in the example of FIG. 4. As illustrated in the examples of FIG. 1 and FIG. 4, the various cassettes may have a plurality of stacking positions as they are gradually moved on the rack through the storage position.

The placement mechanism (322) that allows the movement of the cassette from a storage position to a stacking position may, for example, be a piston or hydraulic cylinder linked to the rack or to each cassette, for example, with a pusher like a mechanical finger or a grasper like a jaw. In one embodiment of the present disclosure, the placement mechanism (322) may be configured to linearly move the cassettes from their stacking position to the storage position. As an example, the loading device (20) may comprise a rail on which the cassettes are placed in their storage position. The rail may be gradually moved through the stacking position by the placement mechanism, pushing the disposable cassettes from their stacking position to the storage position.

In one embodiment of the present disclosure, the shifter may be configured to linearly shift the cassette from its storage position to its connected position. Alternatively, in embodiments when the shifter comprises a connector, the shifter may be configured to linearly shift the cassette from its storage position to the loading position, and the connector may be configured to linearly move the cassette from the loading position to the connected position. These linear movements may be simple movements, which do not require a complex arrangement between the various mechanisms and/or devices that are able to move the cassette from one place to another. It may ensure a more robust device, and may allow better movement accuracy. As an example, the shifter, and the connector, if present, may both be a piston or a hydraulic cylinder, e.g., actuated by automation with a computer.

In one embodiment of the present disclosure, the shifter (32) may be further configured to place a positioning wedge (15) on the connector when the shifter (32) is shifting a cassette from its storage position to the loading position. The wedge may allow for finely positioning at least a part of the connector (321) that will be in interaction with the cassette. The interaction between the cassette and the connector (321) may therefore be more secured and/or easier. It may ensure that the connection movement operated by the connector is precise and accurate, allowing a better interaction between the cassette and the interface (11) after the connection movement. This embodiment is, for example, illustrated in FIG. 5. As depicted, both the shifter (32) and the connector (321) may be hydraulic cylinders. The connector (321) may comprise a first movable part configured to interact with the cassette, and a second fixed part. The first part and the second part may be linked by the hydraulic cylinder that allows the movement of the first part. When the shifter is shifting the cassette to the loading position, it may also place the positioning wedge (15) between the first part and the second part. The connector may then be retracted, e.g., the hydraulic cylinder may be actuated to move the first part through the second part. The wedge may be dimensioned to allow the first part to be placed exactly where it is able to interact correctly with the cassette once the cassette reaches the loading position. When the cassette is located on the loading position, the connector may interact with the cassette in a secure manner, thereby avoiding any damages to the cassette. The shifter may then be actuated backwards, removing the wedge from the connector. Finally, the connector may be actuated to connect the cassette to the interface (11).

In one embodiment, the connector may further comprise an interacting mechanism configured to interact with the positioning mechanism located on the cassette. This interacting mechanism may allow for an improved interaction between the cassettes and the connector (321), improving further the accuracy of the movement of the cassette from the loading position to the connected position. A positioning mechanism may be, for example, a groove configured to interact with a rod located on the disposable cassette. Alternatively, a groove may be located on the cassette, and the positioning mechanism may be a rod. Similar mechanisms may also be implemented by one of ordinary skill in the art.

In one embodiment of the present disclosure, the various mechanisms and/or devices for moving the cassette from any position to another position may be actuated by automation with a computer. In other words, the various moving mechanisms and/or devices may be linked to a computer, the computer configured to command the operations enabling the movements of the plurality of cassettes. This may allow an automatic actuation of the different mechanisms and/or devices to ensure a correct sequence of actuation of each mechanism and/or device to move, successively, each cassette located on the loading device to the interface, and eject it after each synthesis run. The computer may comprise one or more dedicated software programs to execute these actuation sequences.

In another aspect of the present disclosure, the apparatus may further comprise a plurality of cassettes. Each cassette may comprise at least one shoulder configured to fit into grooves located on the loading device (20), the placement mechanism (322) being configured to translate at least one cassette through the grooves. This may ensure a correct movement of the cassette from a stacking position to the storage position or to another stacking position.

The cassette may further comprise dedicated portions configured to interact selectively or universally with the various moving mechanisms and/or devices (e.g., the shifter, the connector, the placement mechanism, the ejector, or the like). As used herein, selectively interacting indicates that a plurality of different portions, each configured to cooperate with only a single moving mechanism or device, are located on the cassette. As used herein, universally interacting indicates that a single portion located on the cassette is configured to cooperate with all the moving mechanisms and/or devices. As an example, the moving mechanism may comprise grooves, and the cassette may comprise a rod. The various moving mechanisms and/or devices may all be configured to translate the cassette through the groove for moving it from one location to another location via its interaction with the rod located on the cassette. Other mechanisms and/or device may also be implemented by one of ordinary skill, like a plurality of graspers.

In one embodiment of the present disclosure, the shifter (32) may further comprise a pusher like a mechanical finger or a grasper like a jaw, a hook and/or a seizer configured to grasp, hook and/or seize a disposable cassette. These mechanisms may be configured to drag or push the cassette through the connected position or the loading position when the shifter is actuated. This may allow an easier movement of the cassette. For example, when the loading device (20) is located on the top of the synthesis device, the grasper may help to properly move the disposable cassette by transmitting a moving force to the disposable cassette. In one embodiment, these mechanisms may be a pusher, like a finger, that pushes downward the disposable cassette through its connection position.

Embodiments of the present disclosure have been described in terms of specific embodiments, which are illustrative only and not to be construed as limiting. More generally, it will be appreciated by persons skilled in the art that the present disclosure is not limited by what has been particularly shown and/or described herein.

Reference numerals in the claims do not limit their protective scope.

Use of the verbs "to comprise," "to include," "to be composed of" or any other variant, as well as their respective conjugations, does not exclude the presence of elements other than those stated.

Use of the article "a," "an" or "the" preceding an element does not exclude the presence of a plurality of such elements.

One embodiments of the present disclosure may also be described as follows:
A synthesis module for the synthesis of chemical compounds, e.g., radiopharmaceutical compounds, said synthesis module comprising a loading module configured to receive a plurality of chemical cassettes having reagents and a transfer mechanism, the loading module comprising a transfer device configured to move the cassettes from a location on the loading module to a location connected to the synthesis module, where an extractor disposed and configured to interact with the transfer mechanism located on the cassette or on the synthesis device.

The invention claimed is:
1. An apparatus for manufacturing radiopharmaceutical products from reagents, comprising:
    a synthesis device including:
        an interface configured to connect to a cassette having the reagents and a mechanism for transferring the reagents,
        an extractor configured to interact with the transfer mechanism of the cassette, and
        an ejector configured to eject a cassette;
    a loading device configured to store multiple cassettes in a storage position; and
    a shifter configured to successively shift the cassette from the storage position to a connected position on the interface, the shifter comprising:
        a transfer device configured to transfer, in a first movement, the cassette from the storage position to a loading position located proximate to the interface, and
        a connector configured to secure, in a second movement, the cassette to the interface,
        wherein the shifter is configured to place a positioning wedge on the connector when the shifter is shifting the cassette from the storage position to the loading position.
2. The apparatus of claim 1, wherein the shifter is, at least partially, located on the loading device.
3. The apparatus of claim 1, wherein the shifter includes at least one of a piston or a hydraulic cylinder.
4. The apparatus of claim 1, wherein the connector includes:
    a first movable part configured to interact with the cassette;
    a second fixed part; and
    at least one of a piston or a hydraulic cylinder configured to move the first movable part.
5. The apparatus of claim 1, wherein the connector is located on the synthesis device.
6. The apparatus of claim 1, wherein the loading device includes a placement mechanism configured to successively place the multiple cassettes from a stacking position to the storage position.
7. The apparatus of claim 6, wherein the placement mechanism includes at least one of a piston or hydraulic cylinder and at least one of a mechanical finger or a grasper.
8. The apparatus of claim 7, wherein the at least one mechanical finger or grasper is configured to move the cassette through the connected position when the shifter is actuated.
9. The apparatus of claim 6, wherein the placement mechanism is further configured to linearly shift the multiple cassettes from the stacking position to the storage position.
10. The apparatus of claim 6, wherein each cassette in the multiple cassettes includes at least one shoulder configured to fit grooves of the loading device, and wherein the placement mechanism places the multiple cassettes by moving the multiple cassettes through the grooves.

11. The apparatus of claim 1, wherein the shifter is configured to linearly shift the cassette from the storage position to the connected position.

12. The apparatus of claim 1, wherein the connector and the ejector are configured to eject the cassette when the cassette is connected to the interface.

13. The apparatus of claim 1, wherein the connector comprises at least one of a rod configured to interact with a groove of the cassette or a groove configured to interact with a rod of the cassette.

14. The apparatus of claim 1, wherein at least one of the synthesis device and the loading device are self-shielded.

15. The apparatus of claim 1, wherein at least one of the synthesis device and the loading device are placed in a shielded environment.

16. The apparatus of claim 1, further comprising:
a computer,
wherein the computer controls at least the shifter and the ejector such that at least the shifting of the cassette and the ejecting of the cassette are automated.

17. The apparatus of claim 16, wherein the computer controls a sequence of actuation of the shifter and the ejector such that each cassette located on the loading device is shifted to the interface and then ejected after each synthesis run.

18. The apparatus of claim 1, wherein the ejector includes at least one of a piston or a hydraulic cylinder.

* * * * *